United States Patent
Fischer et al.

(10) Patent No.: US 8,344,725 B2
(45) Date of Patent: Jan. 1, 2013

(54) DEVICE FOR NONDESTRUCTIVE TESTING OF PIPES

(75) Inventors: Gert Fischer, Wachtendonk (DE); Sven Gwildies, Mülheim (DE); Michael Kaack, Bochum (DE); Alfred Graff, Essen (DE); Ashraf Koka, Düsseldorf (DE); Stefan Nitsche, Mülheim (DE)

(73) Assignee: V & M Deutschland GmbH, Düsseldorf (DE)

( * ) Notice: Subject to any disclaimer, the term of this patent is extended or adjusted under 35 U.S.C. 154(b) by 274 days.

(21) Appl. No.: 12/711,695

(22) Filed: Feb. 24, 2010

(65) Prior Publication Data

US 2010/0219818 A1 Sep. 2, 2010

(30) Foreign Application Priority Data

Feb. 26, 2009 (DE) .......... 10 2009 010 453

(51) Int. Cl.
*G01N 27/82* (2006.01)
(52) U.S. Cl. ......... 324/238; 324/262; 324/220; 367/156
(58) Field of Classification Search ............... 324/238, 324/262, 220; 367/156
See application file for complete search history.

(56) References Cited

U.S. PATENT DOCUMENTS

| | | | | |
|---|---|---|---|---|
| 4,789,827 A | * | 12/1988 | Bergander | 324/220 |
| 5,581,037 A | * | 12/1996 | Kwun et al. | 73/623 |
| 6,593,562 B1 | * | 7/2003 | Parrish et al. | 250/208.1 |
| 2005/0007108 A1 | * | 1/2005 | Dogaru | 324/235 |
| 2005/0264284 A1 | * | 12/2005 | Wang et al. | 324/240 |
| 2008/0042645 A1 | * | 2/2008 | Kaack et al. | 324/220 |
| 2009/0046762 A1 | * | 2/2009 | Henshaw et al. | 374/179 |

FOREIGN PATENT DOCUMENTS

DE 10 2004 035 174 2/2006

OTHER PUBLICATIONS

Nondestructive Evaluation, A Tool in Design, Manufacturing, and Service, CRC Press 1997, Don E. Bray & Roderic K. Stanley, pp. 311-337.

* cited by examiner

*Primary Examiner* — Huy Q Phan
*Assistant Examiner* — Temilade S Rhodes-Vivour
(74) *Attorney, Agent, or Firm* — Henry M. Feiereisen LLC

(57) ABSTRACT

A device for nondestructive testing of a pipe made of ferromagnetic steel for detection of longitudinal, transverse or inclined flaws using magnetic or magnetic-induction test procedures is disclosed. The device includes a magnetizing yoke which transmits the magnetic flux contactless into the pipe and at least two magnetic-field-sensitive scanning probes having GMR sensors. The GMR sensors are combined into sensor groups in form of a sensor array and electrically connected in parallel. A single preamplifier connected to each sensor group in one-to-one correspondence. The device further includes an evaluation unit.

6 Claims, 3 Drawing Sheets

DEVICE FOR NONDESTRUCTIVE TESTING OF PIPES

CROSS-REFERENCES TO RELATED APPLICATIONS

This application claims the priority of German Patent Application, Serial No. 10 2009 010 453.4, filed Feb. 26, 2009, pursuant to 35 U.S.C. 119(a)-(d), the content of which is incorporated herein by reference in its entirety as if fully set forth herein.

BACKGROUND OF THE INVENTION

The invention relates to a device for nondestructive testing of pipes made of ferromagnetic steel using magnetic or magnetic-induction test procedures.

Devices of this type have of a magnetizing yoke which transmits the magnetic flux contactless into the pipe and at least two magnetic-field-sensitive scanning probes implemented as GMR sensors as well as an evaluation unit.

Magnetic and magnetic-induction test procedures, for example the conventional magnetic leakage flux test, are used with pipes made of ferromagnetic steel to detect, in particular, longitudinal, transverse or inclined discontinuities, for example cracks, near the surface which cannot be detected at all or only with great imprecision with other test procedures, which tend to be expensive and time-consuming.

This method can be used to detect, for example, cracks extending from the surface of the pipe into the material by at least about 0.3 mm (Nondestructive Evaluation, A Tool in Design, Manufacturing, and Service, CRC Press 1997).

For example, DE 10 2004 035 174 discloses the use of so-called GMR sensors (Giant Magneto Resistance) in magnetic flaw tests, which have a high field sensitivity at low frequencies, are quite immune from electrical interference and can therefore also be employed, unlike conventional Hall sensors or induction coils, at greater distances from the test surface.

A comparison between inductive sensors (coils) for flaw detection and GMR sensors shows that GMR sensors have a high sensitivity, a high signal level, a low noise level and a high lateral resolution due to their small dimensions.

The higher sensitivity accompanied by the smaller noise level are advantageous when testing pipes, in particular for detecting interior flaws. The novel GMR sensors are therefore necessary to increase the range of wall thicknesses that can be tested, while simultaneously improving reliability. In addition, the low noise level offers enhanced possibilities for the test strategy.

As a consequence of the high lateral resolution, a single induction coil must be replaced by a plurality of GMR sensors (e.g., 8 elements) in order to be able to cover the same test surface and hence attain the same test performance.

Typically, each GMR sensor, like conventional Hall sensors in existing test systems, is operated with a dedicated difference preamplifier. The downstream evaluation electronics must then be configured with multiple channels.

If the intended test does not require a high resolution, then the number of channels has until now been reduced, due to the sensor properties, by employing an additional processing stage in the electronics or later in the digital section of processing. The test system consequently becomes quite complicated and expensive.

The use of a dedicated preamplifier for each GMR sensor necessitates a large number of components and connections. This complexity is necessary, in particular, if the increased lateral resolution is taken advantage of. Disadvantageously, the overall dimensions of the test unit increase substantially, which may cause problems in confined spaces.

For example, if each of the 8 coils in a test head are to be replaced by 8 GMR sensors having the same test surface, then 64 preamplifier are required instead of the previously employed 8 preamplifiers. In addition, the total number of connections increases from 9 (8+1 common ground) to 128. Due to the small size of the sensors, it is difficult to install this large number of connections in the test head.

It is would therefore be desirable overcome the shortcomings of the prior art and replace a test head for a magnetic or magnetic-induction flaw test having inductive sensors with a test head having at least two GMR sensors in form of an array, and to also reduce the complexity of the mechanical and electronic hardware, while substantially maintaining or even improving the test surface and test performance. Adjustment of the spatial resolution would also be desirable.

SUMMARY OF THE INVENTION

According to one aspect of the invention, a device for nondestructive testing of pipes made of ferromagnetic steel for detection of longitudinal, transverse or inclined flaws using magnetic or magnetic-induction test procedures, includes a magnetizing yoke which transmits the magnetic flux contactless into the pipe and at least two magnetic-field-sensitive scanning probes implemented as GMR sensors and an evaluation unit. The GMR sensors are combined into sensor groups configured as an array, with the sensors in electrically connected in parallel, wherein of an array formed from a combination of GMR sensors electrically connected in a parallel according to the invention.

With the present invention, inductive sensors are replaced with GMR sensors, which have an enormous potential for improving the informative value of tests by, for example, increasing the reliability, offering the possibility to test greater wall thicknesses, improving signal evaluation due to better sensor arrangement, while substantially reducing of electronic and mechanical complexity, primarily by reducing the complexity of the test head compared to a conventional GMR test head which in general employs a dedicated preamplifier for each sensor.

Several GMR sensors can be directly electrically connected in parallel in form of an array. This eliminates the aforementioned disadvantages associated with the complex sensor electronics for each individual sensor in conventional designs.

In one embodiment of the invention, the resolution of the sensor system can advantageously be adjusted by combining sensors into a plurality of subsets.

This design can optimize the spatial resolution and reduce the complexity of the components.

In another advantageous embodiment of the invention, gaps in testing which can be caused by a spatial separation of the sensors, can be reliably prevented by arranging adjacent sensor groups in such a way so that at least one sensor in one group overlaps with a sensor in the other group.

In another advantageous embodiment of the invention, a flaw located at the outside surface area or at the inside surface of a pipe can be unambiguously assigned by not only arranging the sensor group next to one another, but by additionally arranging two sensor groups on top of one another in the radial direction so that all sensors of these two sensor groups overlap.

Commensurate with the process disclosed in DE 10 2004 035 174, the amplitude of the horizontal field component of the magnetic leakage flux, which changes in the vertical direction, is measured, on one hand, at a distance proximate to the outer surface of the pipe and, on the other hand, at a distance farther away, whereby the measured signals are correlated.

In addition, like with coils sensors, the background noise of the signals from the test head equipped with GMR sensors in form of an array according to the invention can be suppressed or filtered by computing the difference between adjacent or more distant sensors. The differences between adjacent sensor groups or the differences between sensor groups located at an arbitrary distance or the differences between sensor groups and a suitable arranged individual sensor can be formed using suitable electronics.

BRIEF DESCRIPTION OF THE DRAWING

Other features and advantages of the present invention will be more readily apparent upon reading the following description of currently preferred exemplified embodiments of the invention with reference to the accompanying drawing, in which.

DETAILED DESCRIPTION OF PREFERRED EMBODIMENTS

Figure 1:
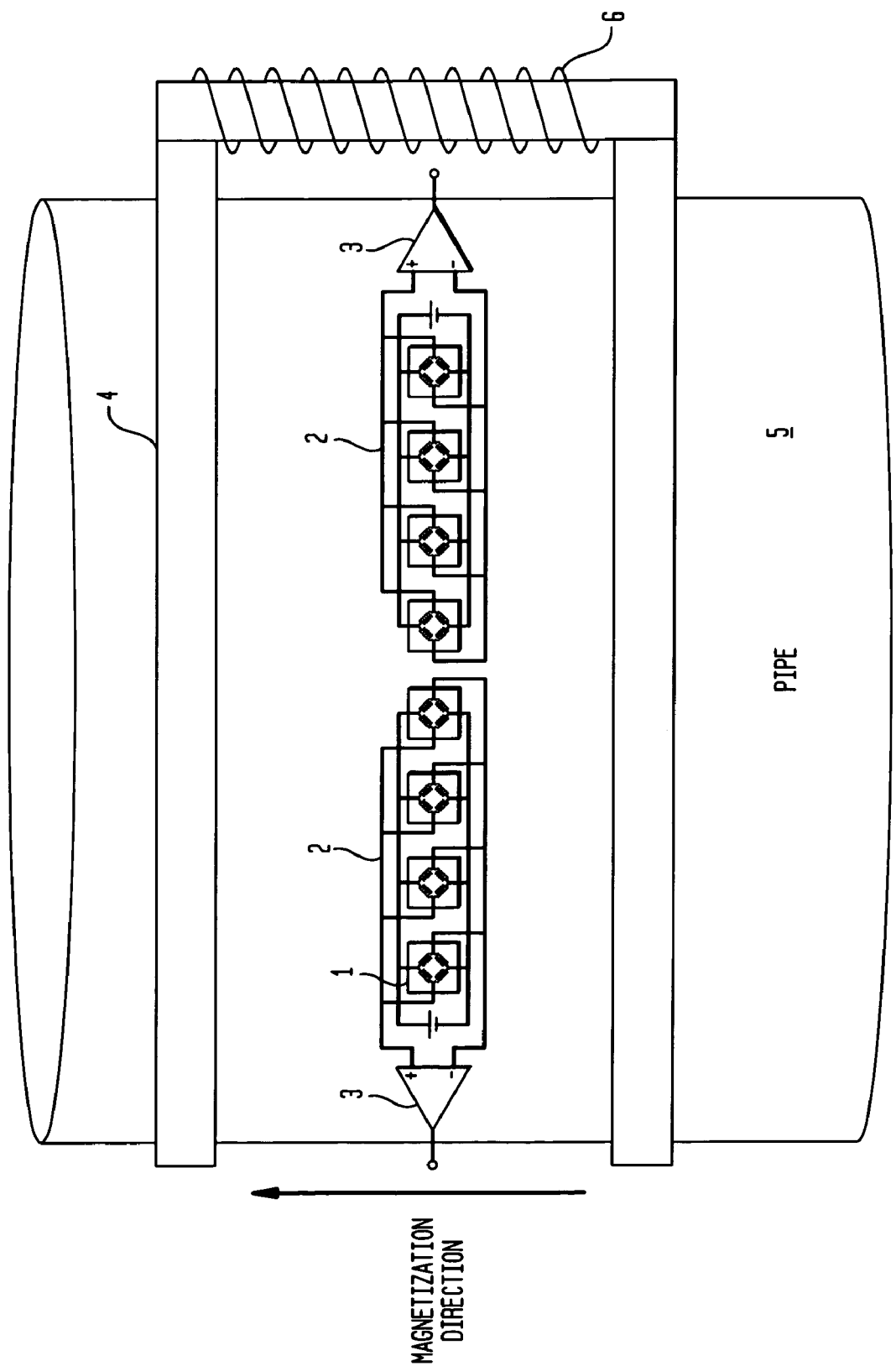
FIG. 1 shows in a top view a schematic diagram of a first embodiment of an array formed from a combination of GMR sensors electrically connected in a parallel according to the invention.

Throughout the Figures, same or corresponding elements are generally indicated by same reference numerals. These depicted embodiments are to be understood as illustrative of the invention and not as limiting in any way. It should also be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted.

Turning now to FIG. 1, there is shown a first exemplary embodiment of an array 2 formed from a combination of GMR sensors 1 electrically connected in parallel according to the invention. The arrow shows the magnetization direction which may coincide with the testing direction of the pipe 5. A magnetizing yoke 4 transmits the magnetic flux, which may be generated by a coil 6 wound around a leg of the yoke 4, contactless into the pipe 6.

A 6-channel inductive sensor system was here replaced by eight GMR sensors 1 which are combined into two sensor groups 2, each having four GMR sensors 1 connected in parallel.

According to the invention, each sensor group 2 has only a single common preamplifier 3, which significantly decreases the number of components.

Figure 2:
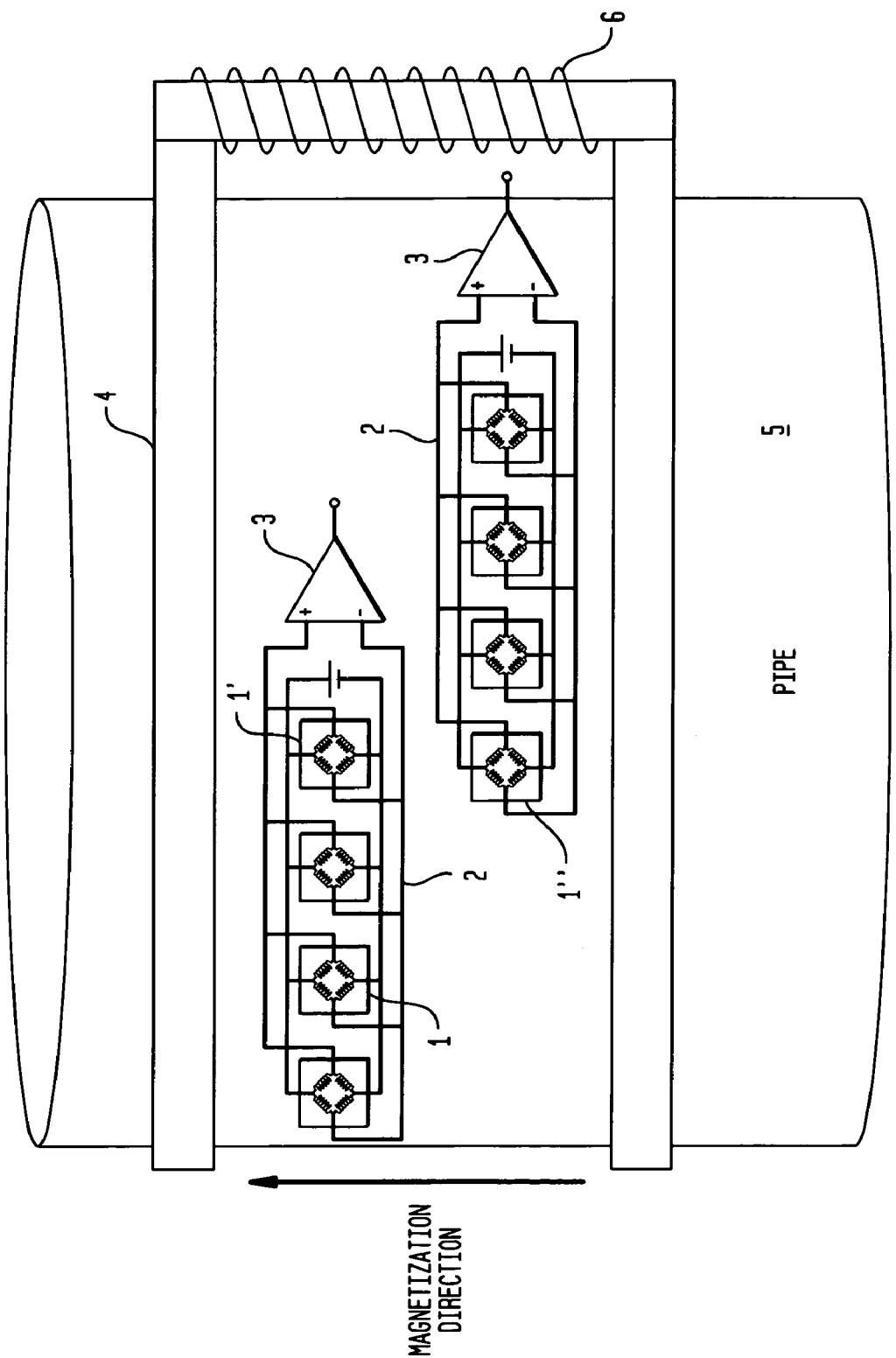
FIG. 2 shows in a top view a schematic diagram of a second embodiment of an array formed from a combination of GMR sensors electrically connected in a parallel according to the invention.

As illustrated in FIG. 2, gaps during the test can advantageously be prevented by staggering the sensor groups 2 with a longitudinal offset and a radial overlap, as viewed in the magnetization and/or testing direction, so that at least one sensor 1' of one sensor group 2 overlaps with a sensor 1'' of another sensor group 2 along a test track.

In the illustrated embodiments, the number of components is reduced compared to the conventional circuit, where the GMR sensors are arranged along a line, by a factor of 4, while the resolution is increased by a factor of 2 compared to a conventional coil system. The orientation of the sensor axis is here selected to be parallel to the test direction (magnetization direction) for identifying transverse and/or longitudinal flaws; however, the sensor axis may also be rotated to increase the sensitivity for inclined flaws.

Figure 3:
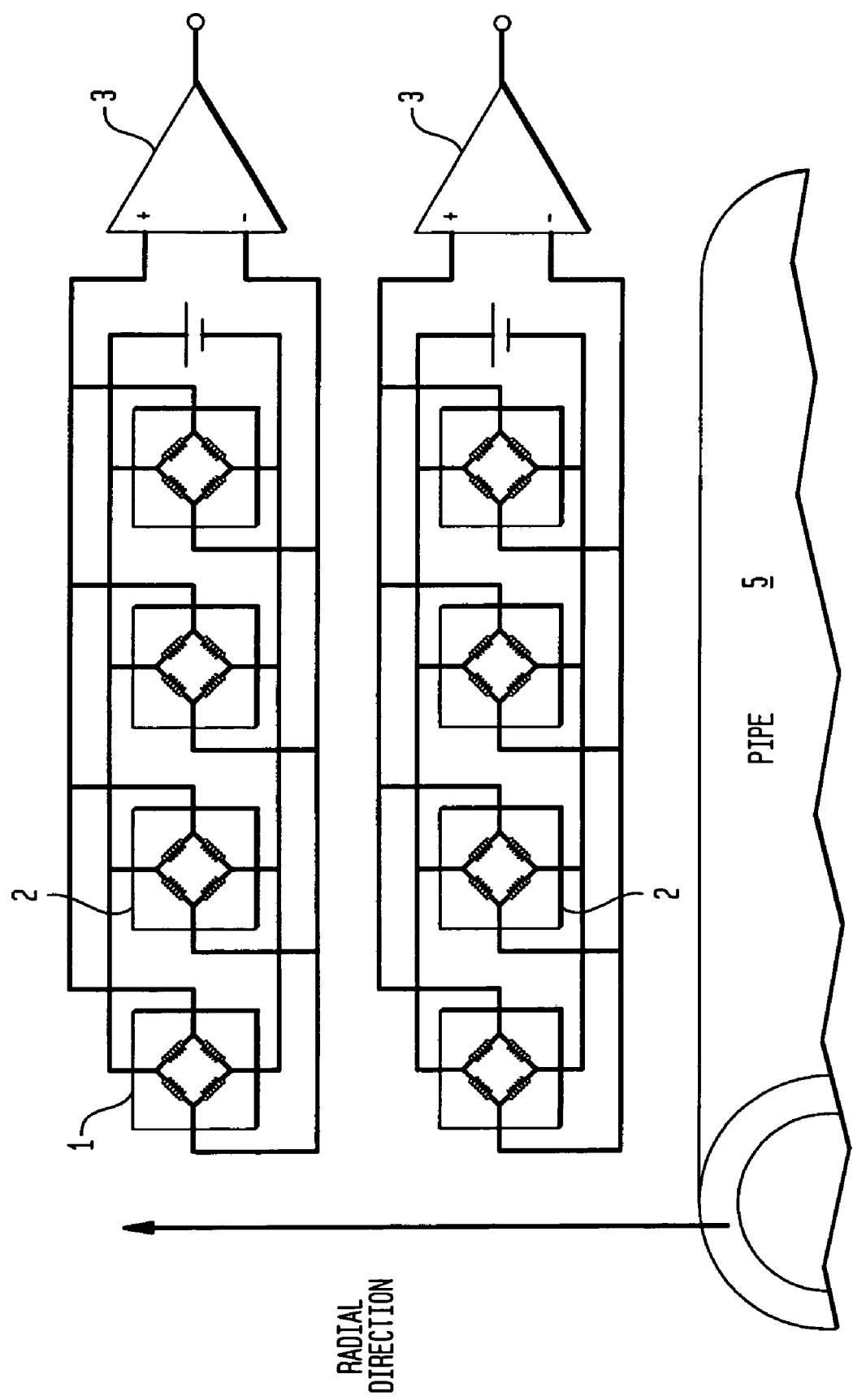
FIG. 3 shows in a side view a schematic diagram of a third embodiment of an array formed from a combination of GMR sensors electrically connected in a parallel according to the invention.

As indicated in FIG. 3, the arrangement of the sensors according to FIGS. 1 and 2 can be modified by arranging two sensor groups on top of one another in a radial direction of the pipe 5, i.e., at different distances from the pipe, with the aim to increase the informative value by forming a difference between the signals from the two sensor groups, with two corresponding sensors each overlapping one another, so that a difference between the respective signals can be computed, as disclosed in DE 10 2004 035 174.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and includes equivalents of the elements recited therein:

1. A device for nondestructive testing of a pipe made of ferromagnetic steel for detection of longitudinal, transverse or inclined flaws using magnetic or magnetic-induction test procedures, comprising:
   a magnetizing yoke which transmits the magnetic flux contactless into the pipe,
   at least two magnetic-field-sensitive scanning probes having GMR sensors, wherein the GMR sensors are combined into at least two sensor groups in form of a sensor array, with the GMR sensors in a sensor group being electrically connected in parallel,
   a single preamplifier connected to each sensor group in one-to-one correspondence, and
   an evaluation unit,
   wherein the sensor arrays of different sensor groups are arranged, as viewed in a test direction of the pipe, sequentially in the test direction and with a mutual offset to one another perpendicular to the test direction in such a way that at least one GMR sensor of an array of one sensor group overlaps in the test direction with a GMR sensor in an array of another sensor group wherein at least two of the sensor arrays are arranged on top of one another in a radial direction of the pipe, so that the GMR sensors of different arrays of the at least two arrays have different distances from a surface of the pipe and sensors of one of the at least two sensor arrays overlap with sensors of another of the at least two sensor arrays.

2. The device of claim 1, wherein the GMR sensors are selectively connected so as to form a subset.

3. The device of claim 1, wherein all of the GMR sensors are connected in parallel.

4. A device for nondestructive testing of a pipe made of ferromagnetic steel for detection of longitudinal, transverse or inclined flaws using magnetic or magnetic-induction test procedures, comprising:
- a magnetizing yoke which transmits the magnetic flux contactless into the pipe,
- at least two magnetic-field-sensitive scanning probes having GMR sensors, wherein the GMR sensors are combined into at least two sensor groups in form of a sensor array, with the GMR sensors in a sensor group being electrically connected in parallel,
- a single preamplifier connected to each sensor group in one-to-one correspondence, and
- an evaluation unit,
- wherein at least two sensor arrays are arranged on top of one another in a radial direction of the pipe, so that the GMR sensors of different arrays have different distances from a surface of the pipe and all sensors of one array overlap with sensors of another array.

5. The device of claim 4, wherein all of the GMR sensors are connected in parallel.

6. The device of claim 4, wherein the GMR sensors are selectively connected so as to form a subset.

* * * * *